(12) United States Patent
Behrends et al.

(10) Patent No.: US 9,671,441 B2
(45) Date of Patent: Jun. 6, 2017

(54) MICROSTRUCTURE DEVICE FOR MEASURING MOLECULAR MEMBRANES AND A METHOD FOR PRODUCING SAID MICROSTRUCTURE DEVICE

(75) Inventors: Jan Behrends, Stegen (DE); Gerhard Baaken, Freiburg (DE); Juergen Ruehe, Eichstaetten (DE); Martin Vellinger, Munich (DE)

(73) Assignee: ALBERT-LUDWIGS-UNIVERSITAET FREIBURG, Freiburg (DE)

( * ) Notice: Subject to any disclaimer, the term of this patent is extended or adjusted under 35 U.S.C. 154(b) by 872 days.

(21) Appl. No.: 13/979,128

(22) PCT Filed: Jan. 10, 2012

(86) PCT No.: PCT/EP2012/000080
§ 371 (c)(1),
(2), (4) Date: Nov. 19, 2013

(87) PCT Pub. No.: WO2012/095298
PCT Pub. Date: Jul. 19, 2012

(65) Prior Publication Data
US 2014/0062503 A1    Mar. 6, 2014

(30) Foreign Application Priority Data
Jan. 10, 2011    (DE) .......................... 10 2011 008 206

(51) Int. Cl.
*G01N 27/327*    (2006.01)
*G01R 27/00*    (2006.01)
*G01N 33/487*    (2006.01)

(52) U.S. Cl.
CPC ....... *G01R 27/00* (2013.01); *G01N 33/48728* (2013.01)

(58) Field of Classification Search
CPC .................. G01N 33/48721; G01N 33/48728
See application file for complete search history.

(56) References Cited

U.S. PATENT DOCUMENTS

| | | | |
|---|---|---|---|
| 8,211,283 B2 * | 7/2012 | Kendig ................ | G01N 27/301 204/435 |
| 2005/0009171 A1 * | 1/2005 | Fertig .............. | G01N 33/48728 435/287.2 |

OTHER PUBLICATIONS

Ogier et al., "Suspended Planar Phospholipid Bilayers on Micromachined Supports," Langmuir 2000, 16, 5696-5701.*

* cited by examiner

*Primary Examiner* — Alexander Noguerola
(74) *Attorney, Agent, or Firm* — Todd A. Lorenz (57) ABSTRACT

The invention is related to a microstructure apparatus for the measurement of biological membranes, comprising a support substrate having an upper side for supporting the membrane, at least one microcavity of the support substrate for receiving an electrolyte, wherein the microcavity is open upward and ends in a microaperture in the upper side of the support substrate, wherein the microaperture has a first characteristic diameter D1 and has at least one electrode, which is at least partially arranged within the microcavity and which has a contact side for contacting an electrolyte, the contact side being arranged adjacent to the inner volume of the microcavity, characterized in that the contact side of the electrode has a characteristic diameter D2, being larger than D1. The invention further relates to a corresponding method for producing the microstructure apparatus.

8 Claims, 6 Drawing Sheets

MICROSTRUCTURE DEVICE FOR MEASURING MOLECULAR MEMBRANES AND A METHOD FOR PRODUCING SAID MICROSTRUCTURE DEVICE

FIELD OF THE INVENTION

The present invention is related to a microstructure apparatus for the measurement of molecular membranes, in particular lipid bilayers, and a method for the fabrication of the microstructure apparatus.

BACKGROUND OF THE INVENTION

Molecular membranes, in particular lipid bilayers (double lipid layers) are used, for example, in membrane biophysics and in cellular electrophysiology as well as in single-molecule analytic methods, which are based on nanopores (molecular Coulter Counter). In these applications the voltage clamp technique ("voltage-clamp") is used in order to obtain an accurate measurement of flows of charged particles (ions). The measurement of the ion current is carried out by using a dielectric (insulating) separation layer (membrane) containing the electrolyte solution between two compartments containing electrolytes, the separation layer comprising at least one ion-permeable pore or ion channel. Said membrane can be a lipid bilayer, which is the typical basic component of natural biological (cell) membranes and can which therefore be used as an artificial model of a natural cell membrane. The voltage clamp technique requires to electrically contact the two compartments, namely, to contact the electrolyte-filled spaces on both sides of the membrane. For this purpose, the membrane is usually formed above the microaperture surface of a support substrate, wherein the microaperture forms the upper edge of a micro-cavity or a micro-hole in the support substrate. Forming the lipid bilayer on said surface will let the molecular layer span the microaperture "self-supporting" by means of its own surface tension. Since these microapertures appear to be "black" in the optical microscope, they are also called "Black Lipid Membranes" (BLM).

For achieving not only a high degree of precision of the measurement (high signal-to-noise ratio) but also a high throughput of voltage clamp measurements, it is desirable to perform such measurements in microstructures, into which the dielectric separation layer is integrated. The smaller the dimensions of the separation layer and the compartments filled by electrolyte, the lower the noise of the electrical measurement, and the more such measurement arrangements can be arranged to a small area in the form of an array. A high density of such arrangements is a precondition for high-throughput measurements.

All the established apparatus for voltage clamp measurements of dielectric separation layers or (cell) membranes are based on the structural principle of that the membrane (cell membrane, synthetic lipid membrane, layer of SiO2, SiN3 layer, graphene layer, or the like) electrically seals a microaperture in a tight manner, which is formed in an electrically insulating support layer, which separates two compartments filled with electrically conductive media (saline electrolyte) from each other. The electrical contact, i.e. the transition from electronic conduction to ionic conduction is effected at one of the two redox electrodes (typically, Ag/AgCl), which extend in each case in one of the two compartments and which are connected via salt bridges. Typically, the electrodes are silver wires having thicknesses between 0.5 and 2 mm and being coated with silver chloride.

In order to bring the electrodes into electrical contact with the membrane, relatively large electrolyte-filled spaces are required, which need space and thus limit the density of integration. In addition, a large surface wetted by electrolyte causes a high electrical capacity of the overall system, which impacts negatively on the capacitive noise of the current and thereby reduces the measurement accuracy (parasitic capacitance).

A rather simplified microstructure for performing voltage clamp measurements on membranes was therefore proposed, respectively, by Baaken, Pruckers, Behrends, Ruehe 2005, European Cells and Materials 5, Suppl. 5, p. CS4; Baaken, Prucker, Sondermann, Behrends, Ruehe 2007, Tissue Engineering 18, 889, or in the document referred to as "Baaken et al" (Baaken et al, "Planar microelectrode-cavity array for high-resolution and parallel electrical recording of membrane ionic currents", Lab Chip, 2008, 8, 938-944). In the microstructure described therein, in contrast to previous procedures, the membrane was not applied onto a microaperture between two compartments, but onto the opening of a cavity, which was introduced into an electrically insulating material (in the form of a blind hole). The electrical contacting of the electrolyte volume ranging between several pL up to several 100 fL within the cavity is carried out in particular at the bottom thereof by means of a microgalvanically formed Ag/AgCl microelectrode (microelectrode cavity arrays, MECA). A similar microstructure apparatus is described by US 2009/0167288 A1.

By means of said simplification, the space requirement for each measuring position is reduced, which allows much higher integration density than before and which, in addition, optimizes the electrical parameters (capacitance, resistance access); additionally, the manufacturing costs can be reduced.

Said promising approach is, however, afflicted with a fundamental problem, which significantly questions its practical suitability for measurements in high-throughput and reliability: in particular for the measurement of large currents, which occur during the measurements on whole cells (being >1 nA, short-term) and during the measurements of nanopores (being >100 pA, continuously), the small sized Ag/AgCl microelectrodes, in particular with a diameter of <50 μm, are not satisfactory stable. This is due to the fact that at small electrode surfaces very high current densities occur, accompanied by the corresponding intensity of the chemical mass conversion at the electrode. Thus, due to the redox reactions and depending on the polarity of the electrode, after a few minutes either an increasingly thick, poorly conducting AgCl layer is formed (in case of the electrode being the anode) or the AgCl is reduced by an amount such that only reduced Ag is present (in case of the electrode being the cathode). In the first case the resistance of the electrode rises massively, and in the second case only a capacitive coupling to the electrolyte is possible according to the principle of a polarizable electrode, and the DC resistance increases abruptly.

A constant, low-drift electrical behaviour of the electrode is desirable. It is an object of the present invention to provide an improved microstructure apparatus and a method for fabricating the same, whose electrical characteristics in an electrolyte during the measurement of a molecular membrane are as stable as possible, in particular on a longer time scale.

SUMMARY OF THE INVENTION

This object is achieved according to the invention by the microstructure apparatus according to the claims and the method according to the claims. Preferred embodiments of the method and the apparatus used by the method are objects of dependent claims.

The apparatus according to the invention for the measurement of molecular membranes comprises: a support substrate having an upper side for supporting the membrane, at least one microcavity of the support substrate for receiving an electrolyte, wherein the microcavity is open upward and ends in a microaperture in the upper side of the support substrate, wherein the microaperture has a first characteristic diameter D1 and has at least one electrode, which is at least partially arranged within the microcavity and which has a contact side for contacting an electrolyte, the contact side being arranged adjacent to the inner volume of the microcavity, wherein the contact side of the electrode has a characteristic diameter D2 being larger than D1.

In case that the microstructure apparatus according to the invention is used, for example, for the measurement on a molecular membrane by voltage clamp technique as described above, it follows that the current flowing through the electrode and the membrane causes a relatively low current density at the electrode, since the contact side of the electrode with the electrolyte has relatively large characteristic diameter. The relatively low electric current density (current/area) of the contact side has the advantage that the electrochemically induced reactions per area per at the contact side of the electrode can be reduced, which would reshape the electrode with respect to time to modify their properties. In this way, the formation of detrimentally thick silver chloride layer (in case of the electrode being the anode), or the detrimentally total removal of the silver chloride layer (in case of the electrode being the cathode) can be delayed, in particular when using a silver/silver chloride electrode. As a result, the electrode has more consistent electrical characteristics, in particular a lower drift and an extended measurement period (before the electrode can optionally be at least partially restored by reversing the polarity again).

A characteristic diameter of a side or surface is understood to be the diameter of a circular area having the same absolute value of magnitude as said side or surface. For example, the characteristic diameter D of a square having a side length a is $D=2*a/\sqrt{\pi}$ and the characteristic diameter D of a circle having the radius $D/2$ is D.

The direction referred to as "upper" or "upwardly" is related, in the present case, to the direction of the normal vector that points away from the microcavity starting from the plane of the microaperture. This direction is also defined to be the direction of the positive z-axis of a Cartesian coordinate system (wherein the origin of this coordinate system is preferably not defined thereby). The direction referred to as "lower" and "downward" is related, in the present case, to the direction of the normal vector that points inside the microcavity starting from the plane of the microaperture (also referred to as the negative direction of the z-axis of the coordinate system). The plane of the microaperture is the plane that is coplanar with the microaperture surface, which is framed by a planar microaperture (microaperture surface). The microaperture is preferably substantially entirely in a plane which runs in particular parallel to the xy-plane of the coordinate system. The microaperture can also extend in more than one plane and can have, in particular, a continuous (stepless) profile.

The characteristic diameter D2 of the contact side of the electrode is preferably larger than $D1*c$ (D1 multiplied by a factor c), wherein c is in each case preferably: 1.1, 1.2, 1.3, 1.4, 1.5, 2.0, 3, 4, 5, 10, 15, 20, 25, 35 or 50. The ratio D2/D1, however, can also be larger. Even at a ratio of D2/D1=1.1, an improvement of the stability of the electrode compared to the case D2/D1=1.0 is observed. It is preferred, in particular, that D2 is at least 1.5 times larger than D1 (D2>1.5*D1) and—preferably—less than 20 (D2<20). This results in particularly suitable electrode properties, wherein the microstructure can be easily fabricated by photolithographic tools. Most stable electrodes resulted at 2.0<D2/D1<20. In case that D1 is kept constant, it must be accepted at ratios D2/D1>20 that the area required for the individual electrode and the measurement position is relatively large, so that the possible density of the electrodes per surface of the support substrate is decreased. Nevertheless, even such large ratios D2/D1 can be advantageous, especially with regard to the stability of the electrode properties.

D2/D1=1 could in principle also be used. Although a simple increase in the diameter of the microcavity, and thus an increase of the electrode forming the bottom of the microcavity and of the microaperture, would reduce the current densities and improve the electrode stability, the problem would not satisfactory be solved, since small microaperture diameters are to be preferred (especially <50 µm) in particular for performing high-resolution measurements using nanopores and microaperture diameters (e.g. <10 µm) are also particularly preferable for measurements on cells.

Preferably, the support substrate comprises a first layer, within which the electrode is at least partially or substantially completely arranged. A layer can be a layer in the support substrate, or a coating of the support substrate. Such a layer is preferably at least partially or substantially completely planar. If the electrode is completely positioned in the first layer, this preferably means that no portion of the electrode protrudes from the first layer or respectively, does not penetrate the imaginary principal planes which envelope the layer for example upwards and downwards. The support substrate may comprise at least one layer, in particular more than two layers or a plurality of layers, wherein the microcavity can be arranged—or not be arranged—in one of these layers, a plurality of these layers or all of these layers.

The first and/or second layer of the support substrate is preferably a coating of the support substrate, which preferably forms its upper side and is preferably hydrophobic, is preferably made of, or comprises, a light-sensitive layer, in particular an epoxy resin or photoresist. The coating preferably consists of a polymer, preferably of epoxy resin or preferably of a photoresist, such as SU8, or includes such a material. The photoresist SU-8 is preferred, because its cured layers are hydrophobic. SU-8 is a commercially available photoresist the company Microchem Corp., USA, and belongs to the group of negative resists. Like most resists SU-8 consists of three components: a base resin, solvents and photosensitive component. These are especially suitable for the production of the microstructure apparatus, especially since many lipid bilayers can form particularly reliable on these resists and since they can be photolithographically processed to produce, for example, microstructures, and since they are relatively chemically inert.

The coating of the support substrate may also preferably comprise polytetrafluoroethylene (PTFE), or consist of said material. The advantage is that such layers are particularly chemically inert, making them especially suitable for use in corrosive environments (e.g. in physiological electrolyte-physiological salt solutions).

Preferably, the microstructure apparatus has at least one wire device, by means of which the electrode means of the distance is electrically contactable across a wiring distance. Preferably at least one wire device is assigned to one (or each) electrode. A wire device may comprise a metallic wire or consist of the same, which can consist, for example, of gold, titanium, nickel-chromium, platinum, or silver, or may comprise one or more of these materials. To distinguish between electrode and wire device it may be defined that with respect to the system including the electrode and the wire device such parts of the system are assigned to the electrode, which contact the electrolyte or the inner volume of the microcavity, while those parts of the system which do not contact the electrolyte or the inner volume of the microcavity are assigned to the wire device. Preferably, the wire device is completely or at least partially arranged in the first layer.

The electrode preferably forms at least a part of the inner wall of the microcavity. The microcavity is preferably formed so that the inner volume of the microcavity is limited by the surface framed by the microaperture and by the inner wall (or a plurality of inner walls) of the microcavity. The at least one inner wall of the microaperture is preferably formed of inner side walls and a bottom wall. The bottom wall of the microcavity is preferably completely or at least partially formed by the contact side of the electrode. The electrode may also be at least partly or completely surrounded by the inner volume of the microcavity. For example, the electrode may be arranged partially self-supporting.

Preferably said first layer is substantially arranged below or at least partially arranged below the microcavity. This allows for a simple fabrication of the electrode, which is preferably arranged below the microcavity.

Preferably, the support substrate comprises a second layer, within which the micro-cavity is at least partially or substantially completely arranged. This allows for a simple fabrication of the microcavity, in particular, which is preferably arranged above the electrode. It is also preferred that the microcavity is at least partially arranged in the first layer, preferably by extending into the same by less than one half or one quarter of its inner volume.

Preferably, the microcavity comprises a second, in particular upper, cavity section, which is defined by the microaperture surface and which (at least at a defined height, or at an average of all the heights) in a cross section of the apparatus has a characteristic diameter D3. Further preferably, the microcavity has a first, in particular lower, cavity section, which is in particular positioned below the upper cavity section and which (at least at a defined height, or at an average of all the heights) in this cross-section has a characteristic diameter D4, and preferably D4 is larger than D3 (D4>D3), namely in particular D4 is larger than D3*c (D3 multiplied by a factor c), wherein c is in each case preferably 1.5, 2.0, 3, 4, 5, 10, 15, 20, 25, 50, and further preferably substantially D4=D2 and preferably D3=D1 (said cross-section passes through the geometric centre of a planar microaperture surface and is perpendicular to the same). A cavity section is preferably substantially cylindrical, the cylinder axis being preferably parallel to the z-axis. A cavity section can also be cuboid-shaped or be designed differently.

The characteristic height H3 of the second cavity section is preferably between 1 μm and 50 μm, preferably between 1 μm and 10 μm or between 3 μm and 6 μm, but may be dimensioned differently. The characteristic height H4 of the first cavity section is preferably between 0 μm and 50 μm, preferably between 0 μm and 10 μm, between 3 μm and 6 μm, more preferably between 0.0005 μm and 1.0 μm or 0.0005 μm and 0.5 μm, or between 0.0005 μm and 0.05 μm, but can also be different. H4 is preferably smaller than H3. The lower cavity section preferably serves for contacting the electrolyte by a relatively large contact side of the electrode, which has a characteristic diameter D2. For this purpose possibly the entire contact side of the electrode should be capable to be contacted, by preferably providing substantially D4=D2, while the height H4 of the lower cavity section does not need to be large for the purpose of electrically contacting the contact side through the electrolyte. Accordingly, H4 can be chosen small. Smaller height values H4 result in smaller distances of the electrode from the microaperture, which is supposed to carry the membrane to be measured. This makes it possible in particular to their use for the voltage clamp technique to improve the signal-to-noise ratio. Further, the microstructure apparatus can be kept particularly compact at small values of H4. It is, however, also possible and preferred that H4 is greater than or equal to H3, since in this case the inner volume of the microcavity will be greater to accommodate a particularly larger quantity of electrolyte, which can be advantageous for certain measurements. Preferably, the first or lower cavity section is located wholly within the first layer and preferably the second or upper cavity section is arranged completely within the second layer. As a result, a cavity section can be fabricated simply by removing the same from the layer, which preferably consists of a photoresist (for example, SU8), by photolithographic means (in particular by using a mask and UV light).

The "characteristic height" H4 (or H3) of the cavity section is preferably an average value. The value preferably results from the fact that to the cavity section a fictitious (cylindrical) volume V is assigned, which is formed by the product of a characteristic circular area A and said characteristic height H4 ($V=A*H4$ or $V=A*H3$). Apart from that, a cavity section can in fact be cylindrically shaped. The characteristic circular area A is obtained from the characteristic diameter D4 (or D3) ($A=(D4/2)^2*pi$). The characteristic diameter of the cavity section is considered to be an average of all characteristic diameters in all heights of said cavity section, which applies, in particular, with respect to a constant lateral dimension or constant diameters of the cavity section, and in particular in the case of varying diameters or in the case of diameters of the cavity section, which vary in dependence on the height. For example, the characteristic diameter $D_k$ of a rotationally symmetrical cone having a diameter D of the circular base surface and a height h $D_k=D/4$ and the characteristic diameter $D_z$ of a cylinder with a diameter D of the circular base surface of the cylinder is $D_z=D$.

A cavity section is understood to be, in particular, a continuous inner volume of the microcavity, which can be filled in particular with water or an aqueous electrolyte. It has been found in experiments that, surprisingly, in particular, low or very low heights H4 (such as 0.0005 μm<H4<0.5 μm) are sufficient to electrically contact an electrode having a relatively large characteristic diameter D2>D1. This has been achieved in particular by such volumes of the second cavity section, which are defined in particular by an open-pore or sponge-like filling material, by having the volume be defined by the inner volume of the continuous pores. The second space section may be defined by an open-pore or sponge-like filling material. This second volume of the cavity section may be surrounded, for example, by the electrode and by the inner wall portions, which are defined by the support substrate and which can be cylindrical-shaped, and by the underside of the first cavity section.

Preferably, the contact side of the electrode has a contact interface with the inner volume of the microcavity, which is non-planar at least within a section (or all) of the interface, and in particular with respect to a microscopic or nanoscopic scale, wherein this contact interface is greater than the surface of the macroscopically planar contact side in this section. This can be achieved through projections (strip-shaped, patch-shaped, plateau-shaped) or depressions (groove-shaped, hole-shaped, channel-shaped) of the contact side. It can further achieved by microstructuring (having characteristic distances of the surface structures in the range of 1 μm to 1000 μm), or by nanostructuring (having characteristic distances of the surface structures in the range of 0.5 nm to 1000 nm) of the contact side of the electrode, or by a material property of the contact side (for example the roughness, porosity, especially micro-porosity or nanoporosity, as in the case of a Ag/AgCl electrode). By way of increasing the electrode interface, the current density (electric current/electrode interface) at the electrode can be reduced and the electrode can be kept more stable, during operation of the electrode, such as in the case of a measurement assembly for the voltage clamp technique of the microstructure apparatus.

It has also been found that, in particular electrochemically produced electrodes made from the material of silver/silver chloride (Ag/AgCl) have as a typical characteristic a nanoporous layer, which forms a continuous inner volume, which is filled, in particular, with an electrolyte, which may be arranged in the microcavity. Thus, a second cavity section with characteristic height H4 and characteristic diameter D4 can be assigned to the nanoporous layer. The nanoporous layer consists of nano-porous AgCl or comprises AgCl. Typical particle sizes of the nano-porous layers are 50 nm to 500 nm. An Ag/AgCl-electrode is preferably produced by electrochemical deposition from a silver nitrate solution. Further details can be found for example in the document "Baaken et al.". The porosity is the result of a standard micro-electroplating, during which the silver is electrode-posited on a seed layer such as gold. The porosity depends on the electrical parameters (current, voltage), time and concentration of the electrolytes used (silver nitrate solutions). Using slight variations, such as higher concentrations of silver nitrate solution, the deposited "Silver Crystals" will be significantly greater.

It should be noted that the volume and the height of said second cavity section will change during operation of the microstructure apparatus when said microstructure apparatus comprises an electrode, which changes in the electrolyte in dependence on the electrical polarity of the electrode. This applies in the case of Ag/AgCl electrodes, as explained above. But since also the nanoporous AgCl, which increases on the electrode in dependence on the polarity or decreases, is sufficiently open-(nano)porous, thus forming a sufficiently continuous inner volume, substantially the entire electrode surface with a characteristic diameter D2 remains in electrical contact with the electrolyte, when a second cavity section, which at the begin, e.g., was hollow-cylinder-shaped, is afterwards substantially completely filled by the nanoporous material.

The support substrate is preferably at least partially or substantially entirely formed planar. The support substrate comprises one or more micro-structures, i.e. spatial projections and/or depressions of small dimensions, for example, said microcavities, which can be, for example a few nanometers, a few micrometers, a few tens of micrometers or a few hundred micrometers. Such microstructures may be produced for example by known optical lithographic methods, in which structures defined by optical masks are applied in layers on a support substrate and partially removed.

The support substrate preferably has an upper side, which is preferably at least partially or substantially completely planar. The upper side preferably comprises at least one microaperture, preferably a plurality N of microapertures, N in each case preferably between 2 and 2000, larger than 2000, preferably between 2 and 400, between 4 and 100, between 4 and 50 or between 4 and 20. On top of a microaperture, a "self-supporting" molecular membrane (BLM), for example, a lipid bilayer be made. This is known, for example, by "spreading" ("coating method", "painting") of a first solution of solvent (such as hexane, heptane, octane, nonane, decane, hexadecane, or other alkanes, or a mixture of one or more of these materials) including said lipid, in a concentration of, for example, 1 mg/ml, to the support substrate on top of the microaperture. Then, the self-supporting molecular layer separates two compartments from each other, allowing measurement setups for realizing a voltage-clamp technique. The use of several microapertures and microcavities has the advantage that several of these sensor systems can be operated in parallel, which allows a higher measurement throughput.

Such a membrane can be a molecular layer of amphiphilic molecules, especially lipids, or consist thereof. The layer may in particular be a double layer, that is composed of two superposed individual layers, wherein a single layer consists in particular of self-assembled molecules. Such molecular membrane can be produced artificially, in particular, a bilayer of lipid molecules can be prepared by means of painting, be prepared by vesicle fusion or by the Langmuir-Blodgett/Langmuir-Schäfer-technique. Such artificial lipid membranes are often used as models of natural membranes. They serve for example as an environment for the study of membrane proteins, which, for example, serve for transporting charges through the membrane positioned to separate two compartments. Such a membrane may also be a natural, biological membrane, which is applied over at least one microaperture. This can be accomplished by using a substantially planar portion ("patch") of the membrane of a biological cell, or by using a complete, treated or untreated biological cell, resting on said at least one microaperture. The thickness of the molecular layer, in particular, has molecular size, and may be between 1 nm and 100 nm.

A microaperture is understood to be the open cross-section, which results, for example, by providing an opening, such as a recess or a hole in an—in particular planar—upper side of the support substrate. The shape of the contour of the microaperture is preferably circular, ellipsoidal, triangular, quadrilateral or polygonal shaped. The maximum, minimum or average diameter of each individual microaperture is preferably less than 1000 μm and preferably between 500 nm and 500 μm, preferably between 2 μm and 250 μm, preferably between 2 μm and 50 μm, preferably between 2 μm and 10 μm or between 5 μm and 150 μm. With respect to such preferred microaperture sizes (microapertures) a molecular layer may be formed over the microaperture, which would usually not be possible by using macroscopic apertures having diameters of several millimeters.

Such microapertures can be fabricated by means of optical lithography, by selectively removing a photosensitive layer, such as photoresist, which is mounted on the upper side of the support substrate, which is described, for example, by the document "Baaken et al." or by US 2009/0167288 A1. The microaperture can also form the edge of a hole which extends from the upper side to the lower side of the support substrate. This can be achieved by chemical etching or by irradiation with laser or other high-energy rays, for example.

The arrangement of the number N of microapertures preferably corresponds to an array, preferably a periodic lattice, wherein the position of the microapertures or microaperture-centres can be described by one or a few grating parameters. The arrangement of a periodic lattice has advantages for designing a parallelized sensor system, wherein many as possible of the same measurement points should be created. However, the microapertures may also be arranged in a non-periodic or not completely periodic pattern.

The support substrate is preferably made of glass or comprises glass. But it can also consist of a semiconductor material or at least comprise the same, e.g. Si/SiO2. Other materials are also possible. The upper side of the support substrate preferably has a coating. This is preferably hydrophobic, but may also be hydrophilic. The advantage of a hydrophobic upper side is that many types of lipid bilayers can be formed particularly reliable on such surfaces.

In the context of the present invention, a "hydrophobic" boundary layer is understood to be a layer on which a water droplet has a contact angle of at least 70°, preferably 80°, 85° or 90°, preferably between 80° and 130° or between 90° and 120°. In this respect, the present definition of the term "hydrophobic" is broader compared to the common definition in the literature, where the term usually refers to contact angles greater than 90°. Such contact angles (interior angle of the water droplet on the substrate) can be easily measured using commercially available contact angle measurement devices or by light microscopic evaluation of cross-sectional images of the droplets (using room temperature, standard conditions). In case of a hydrophilic boundary layer, the contact angles are each preferably between 70° and 0°, 80° and 0°, 85° and 0° or 90° and 0°.

Preferably, a supporting substrate has at least one microcavity, or, preferably, an array of micro-cavities, wherein one or each microcavity is open upwardly and ends into one of said microapertures in the upper side of the support substrate. The molecular membrane to be measured can then be formed such that it covers at least one microaperture or more microapertures. A microcavity is a well in the upper side, the depth of which may have the same size as a preferred microaperture diameter described above, or may be deeper or shallower. Each cross-section of the well (in a plane parallel to the plane of the microaperture) preferably has the same cross section as the microaperture, which opens the microcavity upwards. The microcavity can be particularly cylinder-shaped or cuboid-like. It can also shaped like a hollow (truncated) cone or may have a different shape with varying cross-section.

The microstructure apparatus is preferably configured to be a measurement arrangement or a part of a measurement arrangement. Such a measurement arrangement, preferably, comprises the microstructure apparatus and at least a first compartment, namely, a region of space or a chamber. A microcavity can serve as a "second compartment" of a measurement arrangement. The microstructure apparatus preferably further comprises at least one wall portion, which is arranged above the support substrate and which defines the chamber and the first compartment in combination with the support substrate or its coating (s), in which first compartment a volume of liquid of some microliters and preferably up to one milliliter can be placed. Thus, the microstructure apparatus can have a chamber section for accommodating a portion of such a volume of liquid, in particular a first and a second solvent (electrolyte). The first and second compartment are connected to the at least one microaperture. The compartments can be separated, in particular electrically separated, by a membrane, which is arrangeable above the microaperture, such as a lipid bilayer. This membrane separates the electrolyte-filled compartments electrically tight from each other. Preferably, an electrolyte for contacting the lower side of a molecular layer formed on the microaperture is arrangeable or arranged within the second compartment. In the microcavity, the electrode is preferably arranged, by means of which the electrolyte is electrically contacted in the second compartment (corresponding to the arrangement in FIG. 1). Further preferably, at least one counter electrode is arranged in the first compartment, in which an electrolyte is arranged or can be arranged. Using this measurement arrangement having the microstructure apparatus, a measurement arrangement for a voltage clamp technique can be realized.

Preferably, the measurement arrangement, or the microstructure apparatus, has at least one sensor device, which especially has a sensor for performing electrophysiological studies on the molecular layer, in particular lipid bilayer. The sensor device may comprise said electrode in the second compartment, which is arranged on the cis-side of the microaperture at the support substrate and may further comprise at least one further electrode (counter electrode) on the other side of the microaperture, which is arranged in the first compartment in the electrolyte above the molecular layer. Such an electrode is preferably a redox electrode, preferably a redox electrode of "second kind", for example, an Ag/AgCl electrode or a calomel electrode. The electrode is preferably a non-polarizable electrode which allows an easy transition of the ionic charges in the electrolyte to the electronic charge carriers in the metal. For this purpose, preferably Ag/AgCl electrodes are used, preferably in combination with measurement solvents (electrolytes) containing chloride ions.

This sensor device is preferably configured to implement the voltage clamp technique, by means of which in the case of constant voltage flows some smallest currents in the nanoampere scale can be measured including, in particular the picoampere scale, for example using a voltage-clamp amplifier or a patch-clamp amplifier (e.g. an Axopatch 200B, Axon Instruments, Foster City, Calif., operated in the "resistive feedback mode"). The sensor means may comprise an array of sensors that can be arranged in the support substrate or on its surface.

For use as a solvent, namely, the electrolyte, which is placed below and/or above the membrane (molecular layer), in particular a salt solution is suitable, including in particular physiological saline solutions allowing for the electrophysiological measurement of the molecular layer, such as lipid membranes and charge transporting pores, such as channel proteins, contained therein. Suitable solvents, especially for carrying out measurements by means of voltage clamp technique are described, for example, by the document "Baaken et al." or by US 2009/0167288 A1.

Suitable amphiphilic molecules to produce the molecular layers are especially lipids, in particular lipids suitable for the formation of membrane-like lipid bilayers such as, for example, inter alia, described in the document "Baaken et al." or US 2009/0167288 A1.

Preferred embodiments of the device according to the invention can subsequently also taken from the description of the method according to the invention and vice-versa.

The method according to the invention for the fabrication of a microstructure apparatus according to the invention comprises at least the following steps, in particular, without determining the order of the steps: —providing a support substrate, —applying at least one electrode on the support substrate, —applying a (structurable) layer, in particular the second layer, above the support substrate, —forming the at least one microcavity by selectively removing portions of the (structurable) layer, which portions form the microcavity, at least in part or completely.

Preferably, the method comprises the step that the (structurable) layer is formed directly on the support substrate, or on a layer of the support substrate. Alternatively, the method comprises the step, that the patternable layer is indirectly formed on the support substrate, by providing that this structurable layer is first formed on a second separate support substrate and then transferred from this second support substrate to the first support substrate or a layer on the support substrate (preferably by means of "bonding", as explained in the document "Baaken et al.").

Other characteristics and features of the microstructure apparatus and for fabricating the microstructure apparatus, materials, methods, measurement systems and examples of measurements on membranes can be taken from the document "Baaken et al." or from US 2009/0167288 A1.

Further preferred embodiments of the method according to the invention and the microstructure apparatus according to the invention will become apparent from the following description of embodiments in connection with the figures. Identical reference numerals denote substantially identical components.

DETAILED DESCRIPTION OF THE INVENTION

Figure 1:
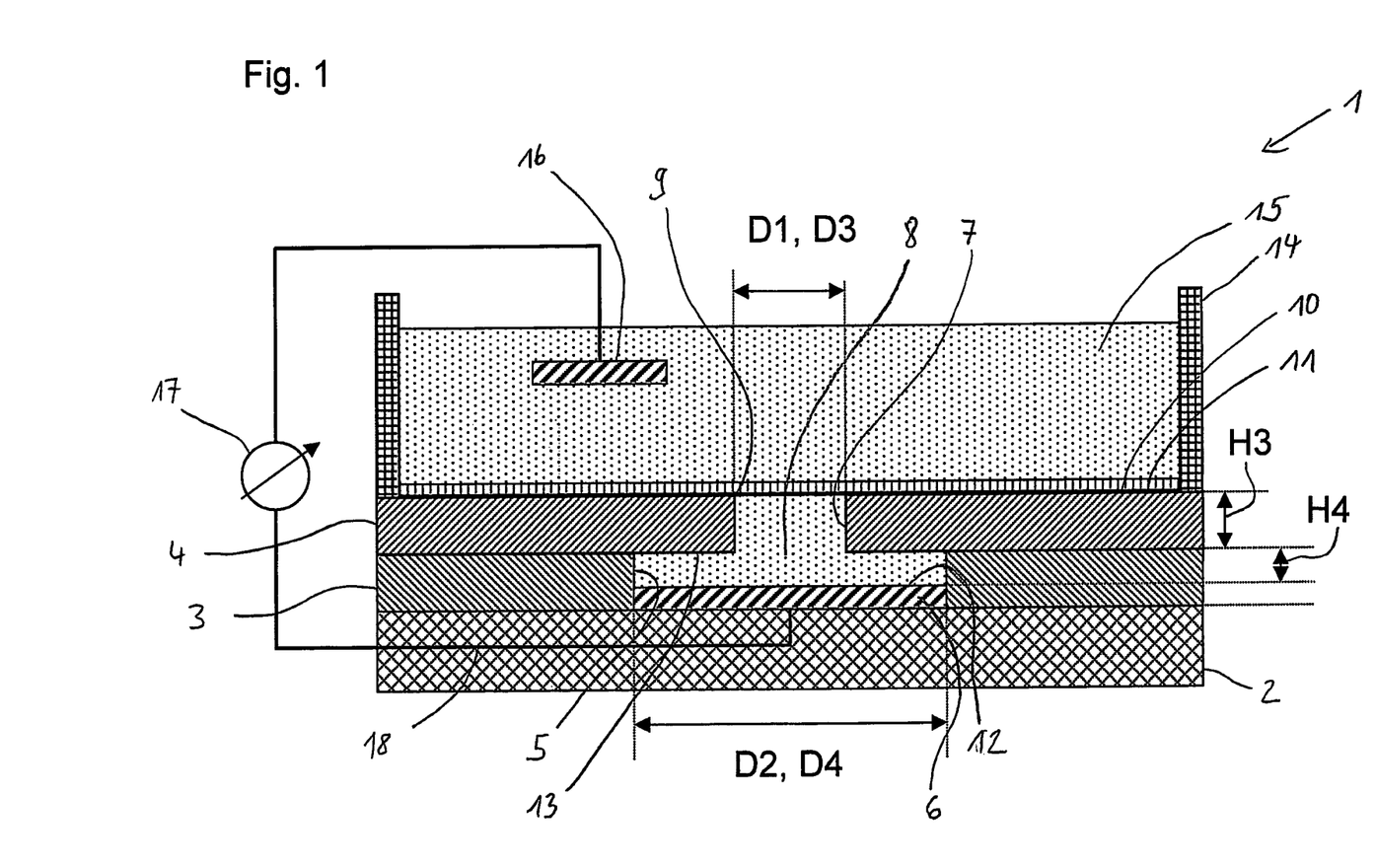
FIG. 1 schematically shows a first embodiment of the microstructure apparatus according to the invention for measuring a membrane in a schematic, vertical cross-section.

FIG. 1 shows the microstructure apparatus 1, which is configured to be a measurement arrangement for the electrophysiological measurement of a membrane 11, namely a lipid bilayer, by means of the voltage-clamp technique. The microstructure apparatus 1 comprises a support substrate 2 made of glass, on which a first layer 3 of photoresist (SU-8) was applied by spin coating (spin coating). The first layer 3 comprises a hollow cylindrical recess 5, which has been produced in particular by a photolithographic method and inside of which, on top of the substrate 2, a redox electrode 6 is mounted. Above the first layer 3 a second layer 4 of photoresist (SU-8) is applied by spin-coating (spin coating) of the liquid photoresist on the first layer 3. The step of producing the second layer of epoxy resin on a first layer of epoxy resin by spin coating, the first layer being in particular already microstructured, in particular comprising the recesses 5, has been found to be surprisingly successful. The second layer is firmly connected, i.e. non-destructively separable connected to the first layer and forms a planar upper side 10 of the microstructure apparatus or the extended support substrate extended by the layers layers 3, 4, which carries the membrane. The second layer 4 comprises a hollow cylindrical recess 7 which in combination with the recess 5 forms an inner volume within the composite layer comprising the first layer 3 and second layer 4. The inner volume of the microcavity 8 is defined by the recess 5, which is the first cavity section, and by recess 7, which is the second cavity section. The inner walls of the recesses 5 and 7, the layers 3 and 4, a portion 13 of the lower side of the second layer and the electrode's contact side 12, which serves as the bottom, define the microcavity 8 and serve as a first compartment 8, or respectively, as a chamber 8 for a liquid electrolyte.

The upwardly open microcavity 8 ends at its top in the microaperture 9, which is arranged in the planar upper side 10 of the microstructure apparatus and which has a circular area of the microaperture 9 having the diameter D1. D1 is the characteristic diameter of the microaperture 9.

The electrode 6 has the shape of a narrow cylinder and is arranged with positive-fitting in the region of recess 5 in the microcavity 8. The contact side 12 is adjacent to the inner volume of the microcavity 8 in order to allow the electrical contacting of an electrolyte placed in the microcavity. The contact side 12 of the electrode 6 has a diameter D2. D2 is the characteristic diameter of the contact side 12 of the electrode 6. D2 is about three times larger than D1. Using said microstructure apparatus 1 for the measurement on a molecular membrane 11 by using voltage clamp technique, it follows that the current flowing through the electrode and the membrane causes a relatively low current density at the electrode 6, as its contact side 12 facing the electrolyte has a relatively large characteristic diameter D2. The relatively low electrical current density (current/area) of the contact side 12 has the advantage that the area per electrochemically induced reactions at the contact side of the electrode is reduced, which reactions may the reshape electrode 6 over time, thus changing its properties. As a result, the electrode has more consistent electrical characteristics, in particular a low drift and a prolonged measurement time.

The first cavity section defined by the first recess 5 and the contact side 12 is hollow cylindrical-shaped and has a diameter D4. D4 is the characteristic diameter of the first cavity section of the microcavity 8. The second defined cavity section second defined by recess 7 is also hollow cylindrical-shaped and has a diameter D3. D3 is the characteristic diameter of the second cavity section of the microcavity 8. Due to the selected geometry for forming the microcavity 8 it is determined that D1=D3 and D2=D4. The first cavity section has a height H4. H4 is the characteristic height of the first cavity section of the microcavity 8. The second cavity section has a height H3. H3 is the characteristic height of the second cavity section of the microcavity 8. Due to the selected geometry for forming the microcavity 8 it is determined that H4<H3. Especially those relatively small values for H4 have proved to reliably contact the electrode 6 with the electrolyte in the microcavity 8.

Located above the upper side 10 of the support substrate 2, wall portions 14 are forming the second compartment 15, which forms a chamber for the liquid-tight receipt of an electrolyte. The first compartment 8 and the second compartment 15 are electrically separated in the region of microaperture 9 through the membrane 11, which tightly rests on the microaperture 9. Using a counter electrode 16, which is arranged in the electrolyte in the second compartment 15, a measurement arrangement for a voltage-clamp technique can now be realized by further use of measurement electronics 17. The microcavity 8 is closed downwards at its bottom by the inner redox electrode 6 (for example, Ag/AgCl). The latter is electrically connected to the sensor electronics 17 of the sensor device by a wire device 18, which may be lithographically produced, for example. In the electrolyte of the chamber 15 is arranged the redox electrode 16, which serves as a reference electrode. By using voltage clamp technique, in which an electric potential across the membrane, for example, using a patch clamp amplifier, is kept constant, lowest amounts of current amendments of a current of charges "q" flowing through the membrane can be detected, which forms the BLM, which spans over the microaperture 9. These charges may be based on the ion transport through the cell membrane or through leaks or be based on pores, such as channel proteins located in the cell membrane.

Figure 2A:
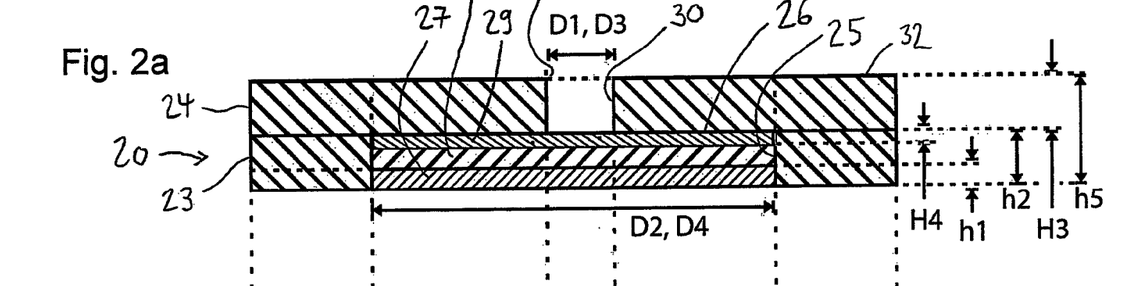
FIG. 2a shows a second embodiment of the microstructure apparatus according to the invention as a schematic, vertical cross-section.
Figure 2B:
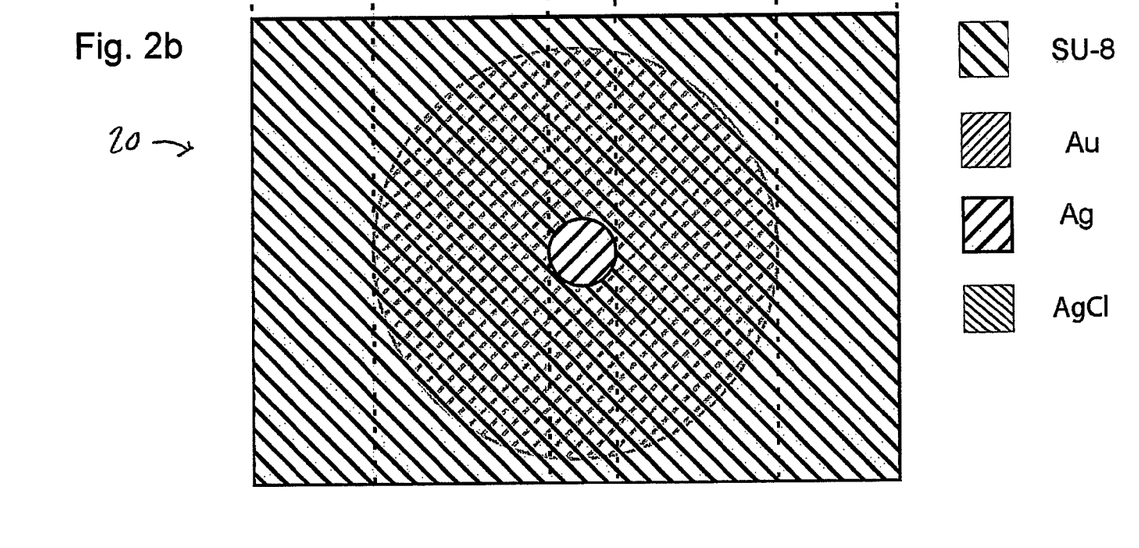
FIG. 2b shows the microstructure apparatus of FIG. 2a as a schematic top view.

FIG. 2a shows a second embodiment of the microstructure apparatus 20. The microstructure apparatus 20 has a support substrate (not shown), on which support substrate the first layer 23 was applied by spin coating of an SU8 photoresist. The first layer 23 comprises a hollow cylindrical-shaped recess 25, which was produced photolithographically. Within the recess 25 the electrode 26 is fitted. The electrode 26 consists of several layers. It has a first layer 27 of gold, which was produced photolithographically, and which contacts the glass support substrate (not shown) and is connected thereto. This layer serves as a starter layer for applying a layer 28 of silver, for example, by vapor deposition. Starting from the layer 28, a layer 29 of silver chloride is formed on the silver layer 28 by electrochemical deposition of silver chloride from a silver nitrate solution. In this way, a silver/silver chloride electrode 26 forms in the recess 25, which serves as a redox electrode for electrically contacting an electrolyte containing chloride ions.

Above the first layer 23, the second layer 24 of photoresist SU-8 is spin-coated. In the second layer 24 the recess 30 is arranged, which ends in the microaperture 31 in the upper side 32 of the extended support substrate, which is extended by layers 23, 24 and which serves to support the membrane.

The inner volume of the microcavity of the microstructure apparatus 20 is formed by the first cavity section, which is defined by the first recess 25 in the first layer 23, and by the second cavity section, which is defined by the second recess 30 in the second layer 24. This may be found surprising, as the first recess 25 is substantially completely filled by the electrode 26. However, it has surprisingly been found that the coherent hollow space or continuous hollow spaces between the pores of the nanoporous silver chloride layer 29, which are connected with the second cavity section 30, define a first cavity section suitable for electrically contacting the electrode 26 by a liquid electrolyte. To said first cavity section can be assigned a characteristic diameter D4 and a characteristic height H4, which differ from the corresponding real dimensions of the silver chloride layer 29, namely being smaller. The silver chloride layer 29 has a composition composed of grains with a grain size of typically 50 nm to 500 nm. The inner volume of the grain interstices forms the volume of said first cavity section. Depending on the polarity of the electrode 26 during operation of the microstructure apparatus, the thickness of the silver chloride layer 29 may change especially in a silver chloride-containing electrolyte, so that the volume of the first cavity section may increase and decrease. It is determined that H4<H3.

Typical dimensions of the microstructure apparatus 20 may be selected, for example, as follows: Characteristic diameter D1 of the microaperture=diameter of the microaperture and characteristic diameter D3 of the second cavity section=the diameter of the second cavity section: D3=D1=3 µm to 20 µm; Characteristic diameter D2 of the electrode=diameter of the electrode and characteristic diameter D4 of the first cavity section=diameter of the first cavity section: D2=D4=10 µm to 100 µm, e.g. 60 µm; total height h5 of the composite layer of the first layer 23 and second layer 24: h5=14 to 20 µm, total height h2 of the electrode 26: h2=7 µm to 10 µm, the height h1 of layer 27 of the electrode: about 0.2 µm, height of the layer 28 of the electrode: 6 µm to 9 µm, height of the silver chloride layer 29: varying, 10 nm to 2 µm.

Figure 3A:
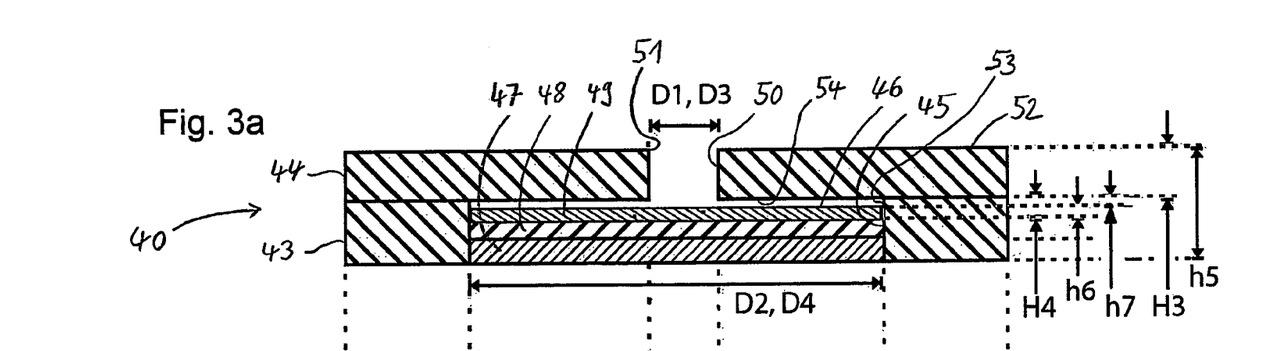
FIG. 3a shows a third embodiment of the microstructure apparatus according to the invention as a schematic vertical cross-section.
Figure 3B:
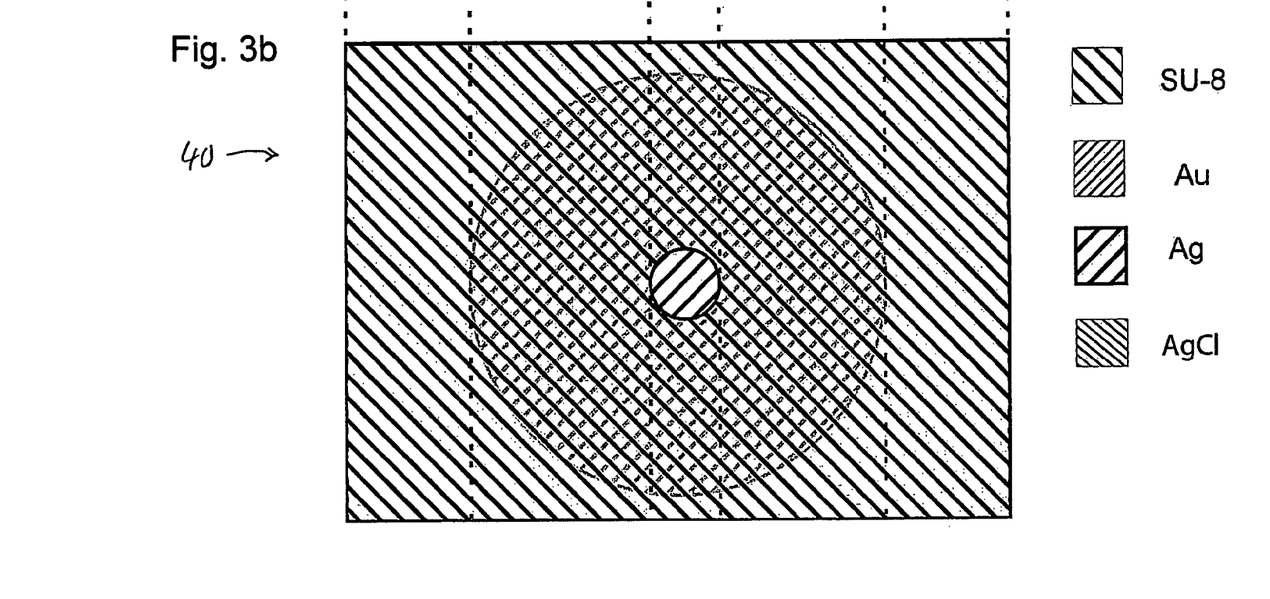
FIG. 3b shows the microstructure of the device 3a as a schematic top view.

FIG. 3a shows another embodiment of the microstructure apparatus 40, which is similar to the microstructure apparatus 20 and was prepared analogously. The microstructure apparatus 40 has a support substrate (not shown), on which the first layer 43 was applied from SU8 photoresist. The first layer 43 comprises a hollow cylindrical-shaped recess 45. Within the recess 45 the electrode 46 is fitted. The electrode 46 consists of several layers. It has a first layer 47 of gold, which contacts the glass support substrate (not shown) and is connected thereto. This layer serves as a starter layer for applying a layer 48 of silver. Starting from the silver layer 48, the layer 49 is formed from silver chloride on the silver layer 48. In this way, a silver/silver chloride electrode 46 is formed in the recess 45, which serves as a redox electrode for electrically contacting an electrolyte containing chloride ions.

Above the first layer 43, the second layer 44 of photoresist SU-8 is spin-coated. The recess 50 is arranged in the second layer 44, the recess 50 ending in the microaperture 51 in the upper side 52 of the extended support substrate, which is extended by the layers of the 43, 44 and which serves to support the membrane.

The inner volume of the microcavity of the microstructure apparatus 40 is formed by the first cavity section, which is defined by the first recess 45 in the first layer 43, and by the second cavity section, which is defined by the second recess 50 in the second layer 44. In contrast to the microstructure apparatus 20, the second space section is not only formed by the nano-porosity of the silver chloride layer 49, to which a characteristic height h6 can be assigned, but also by the free, hollow cylinder-shaped subsection 53 of recess 45, which subsection is formed between the contact side of the electrode 46 facing the inner volume of the microcavity and portions 54 of the lower side of the second layer 44. This subsection has a height h7. Thus, the second cavity section has a characteristic height H4, which corresponds to the real height h7 of the free subsection 53 plus the characteristic height h6 of silver chloride layer 49. By providing the free subsection of section 53, the contact side of the electrode 46 is even more accessible for the electrolyte. It is determined that H4<H3.

In both types of the microstructure apparatus 20 and 40, the stability of the electrodes was significantly improved due to the relatively large electrode area (D2>D1) and, in particular, due to the fact that a higher amount of a nanoporous AgCl material was provided compared to smaller electrodes.

Figure 4:
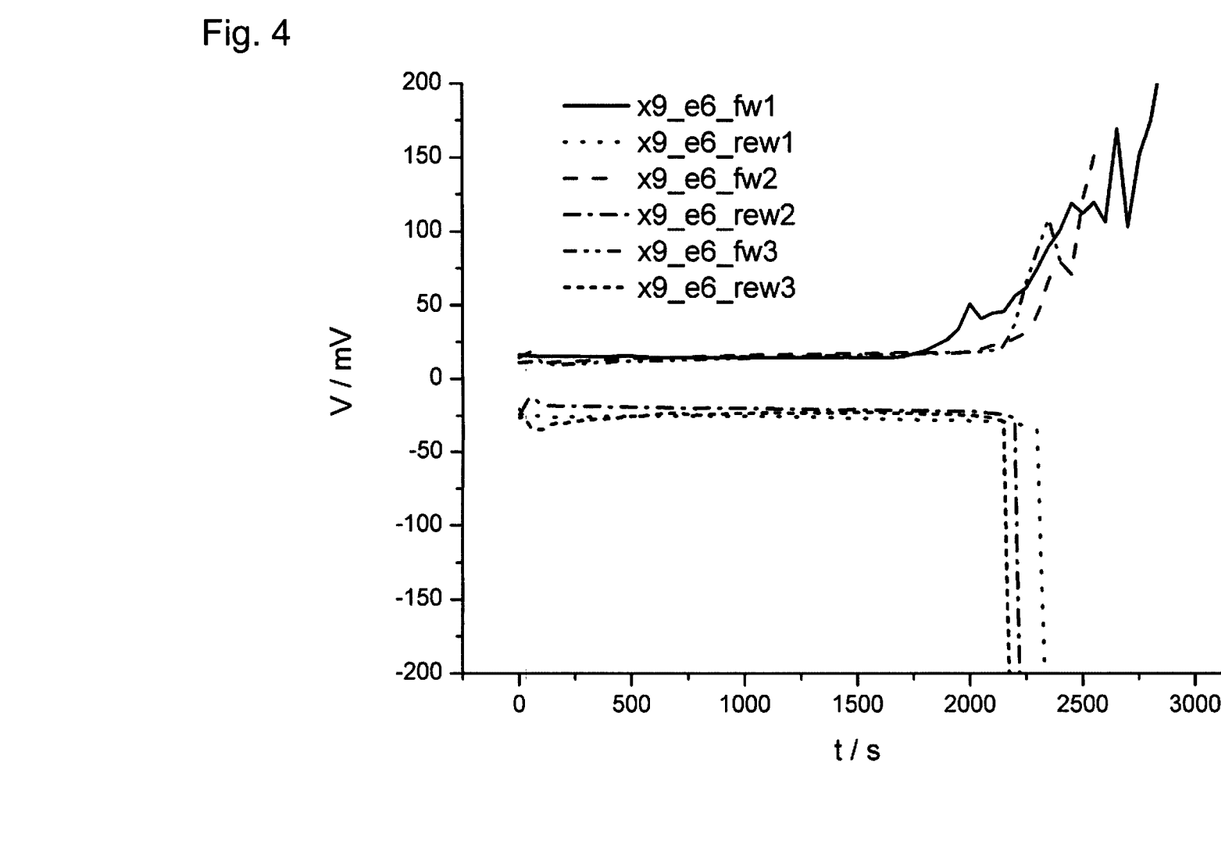
FIG. 4 shows a voltage curve V(t) measured by the microstructure apparatus according to the invention.

FIG. 4 shows a voltage curve V (t) measured by a microstructure apparatus 20 or 40 (with Ag/AgCl electrodes (D2=50 μm)). This is a test of the stability of Ag/AgCl electrodes embedded in an insulator layer (SU8). The graphs describe the course of the required voltage for a constant current of +−10 nA over time.

The electrode was connected as a cathode or an anode for 3 cycles, and was in each case operated until loss of stability. Using the electrodes thus obtained first measurements of very high quality have already been carried out with lipid bilayers that contained alamethicin (see FIG. 5) or botulinumtoxin C2. This showed that the expected improvement of the electrical parameters was fully realized.

In FIG. 4 the voltage over time is shown, which is required for inducing a current of a +/−10 nA. The electrode was switched cyclically between the polarity as an anode and a cathode. In one case, a silver chloride layer grows on the surface, which leads to a significant rise in the voltage needed for a current of 10 nA after a certain time due to the increasing electrical resistance. At this point, the measuring structure has been reversed, that is, the micro-electrode was connected as the cathode. Now, silver chloride at the surface is now reduced to silver. Once no silver chloride is any more available, the resistance and the voltage again rises sharply. The electrode is not stable any more and was again reversed, etc. A total of 3 cycles (forth and back) were performed.

It will be recognized that the electrodes, regardless of whether connected as the cathode or anode, can keep the current constant without a significant deviation in the required voltage, for more than half an hour. It was thus demonstrated that the stability criteria for performing measurements on cells or on highly conductive bacterial pores are easily fulfilled. Using a current of 1 nA will extend, for example, the time available for the measurements in a polarization direction by, for example, about 6 hours. Remarkably, the electrodes can be completely restored after the loss of stability in a polarization direction by operating the same with the opposite driving effect, as is documented by the operation of multiple cycles in FIG. 4.

Figure 5:
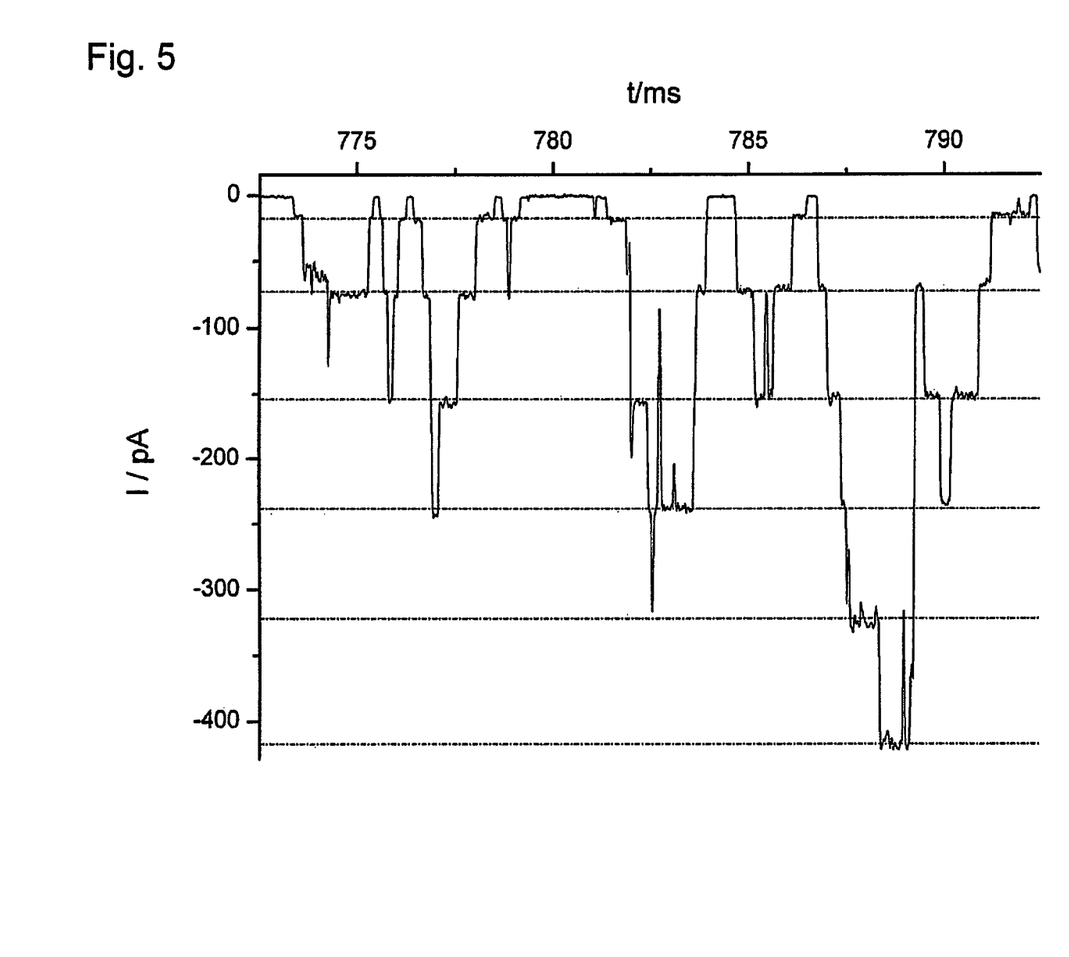
FIG. 5 shows a current curve I(t) measured by the microstructure apparatus according to the invention.

FIG. 5 shows a current waveform I(t) measured by a microstructure apparatus 20 or 40. These are typical current waveforms during voltage clamp using alamethicin-induced currents through a lipid bilayer. The exceptionally high seal resistances (multiple 100 GOhm) should be noted, which were obtained using the SU-8 chips of the microstructure apparatus 20, 40. As a result, the signal-to-noise ratio is significantly improved once again.

Figure 6:
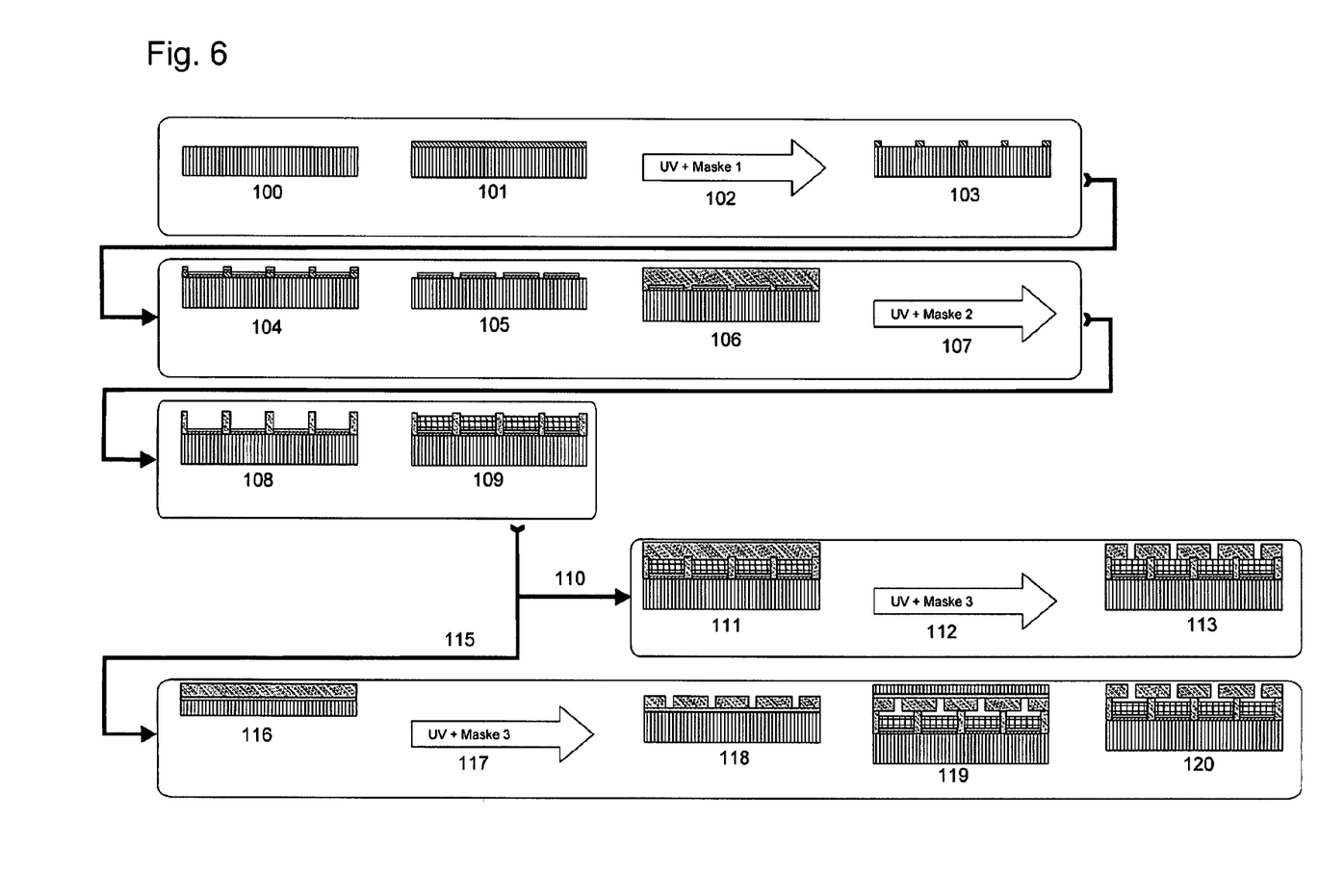
FIG. 6 schematically shows two embodiments of the method according to the invention for the fabrication of the microstructure apparatus according to the invention.

FIG. 6 shows schematically two embodiments of the method according to the invention for the fabrication of the microstructure apparatus according to the invention, in particular for the preparation of such a type of microstructure apparatus 20 or 40, each formed as a multiple electrode in an array assembly. Further details on the preparation of the microstructure apparatus can, for example, be taken from the document "Baaken et al.".

In a first step 100, the planar support substrate is provided, for example, a transparent substrate made of, for example, glass. In step 101 a layer of SU8 photoresist (reverse coating) is applied by spin coating. In step 102 a "mask 1" is placed on this coated support substrate and exposed to UV light. In step 103 the exposed layer is developed and portions of the layer are selectively removed in this way. On top of this microstructure layer, an adhesion-promoting or electroplating starting layer of chromium, gold is evaporated, in step 104. In step 105, the photoresist is removed (stripping, lift-off), which had the support substrate selectively masked for metal vapor deposition, such that a metallic microstructure remains. The latter is coated again by spin coating with photoresist, in step 106. This is the first layer of the support substrate, in which the first recesses 25, 45 (FIGS. 2a and 3a) are formed, in which the electrodes 26, 46 are introduced. This is accomplished by using a "mask 2" which, the step 107, is placed on the photoresist coating and is exposed to UV light. In step 108 the photoresist coating above the chrome-gold areas is selectively removed by developing the exposed photoresist. In step 109 the chromium-gold regions are coated with silver, such that the individual electrodes 26, 46 of the multi-electrode array receive their respective silver layer 28, 48.

Layer thicknesses of, for example, 1 to 200 μm can be achieved by spin coating SU8, which thicknesses are easily set by the viscosity of the photoresist and the rotational speeds. For the first layer and using, for example, D2=60 μm for the electrodes, a thickness of up to 200 μm can be achieved (depending on how much silver is desired to be provided). For the second layer, e.g, 5 to 10 μm are useful in order to allow for the full opening of even small apertures during developing.

For the application of the second layer 24, 44 of photoresist, which ultimately define the microapertures 31, 51, there are two alternative embodiments of the method 110, 115:

The step sequence 110 has been found to be very effective. In this case, in step 111, the second layer of photoresist (SU-8 preferably) was directly spun onto the first layer of photoresist (also preferably SU8), which already comprises the electrode microstructure. It was surprisingly found in experiments that it is possible by the simple spin coating of the polymer (such as epoxy resin, such as SU8) onto the first layer of the same polymer material, to provide a second layer, which is stably connected to the first layer after crosslinking. The materials of the two layers can also be different, as long as a sufficiently stable connection between the two layers is achieved. In step 112, the "mask 3" is placed on the second layer and exposed to UV light. In step 113, the exposed photoresist is selectively removed by development, such that the recesses 30, 50 are formed in the second layer, which constitute the second cavity sections of the microcavities. Thus there is provided a microstructure apparatus, comprising a number N of micro-cavities (eg, N=4 in the figure or, for example, N=16), each microcavity having an electrode.

As an alternative to the process sequence 110, the sequence 115 of method steps can be chosen for applying the second layer containing microapertures on the first layer. For this purpose, a removable sacrificial layer is applied to a separate substrate, for example a glass substrate, and thereon a second photoresist layer (for example, SU8) is spun. In step 117, the "mask 3" is placed on this layer of photoresist and UV-exposed. The exposed photoresist is developed, in step 118, for selectively removing the areas of the recesses 30, 50 (microapertures). In step 119, the second layer is firmly connected with the first layer of preferably the same type of photoresist, by a specific connecting process. This connecting process is known as "thermal bonding". Two (coated) substrates are joined while under high pressure and high temperature. In this case, 150° C. to 200° C. and 2000 to 4000 mbar of pressure can be used. In step 120, the sacrificial layer is dissolved and, in this manner, removed from the second substrate. Thus, an alternative route 115 has been provided for creating a microstructure apparatus having a plurality of microcavities N (e.g, N=4 in the figure or, for example, N=16), each electrode having a microcavity.

By using present invention a reliable and stable platform for the field of high-throughput electrophysiology can be provided and offered at low prices in the market. The possibility of a high integration density and the potential, excellent signal-to-noise ratios offer significant advantages over known devices to the users. The end user is able to measure membrane currents of all kinds quickly and with high throughput. Such measurements play a growing role in the pharmaceutical drug discovery and biotechnology.

The invention claimed is:

1. Microstructure apparatus for the measurement of molecular membranes, comprising
    a support substrate having an upper side top for supporting the membrane,
    at least one microcavity of the support substrate for receiving an electrolyte, wherein the microcavity is open upwards and ends in a microaperture in the upper side of the support substrate, wherein the microaperture has a first characteristic diameter D1,
    at least one electrode, which is at least partially arranged in the microcavity and which has a contact side for contacting an electrolyte, the contact side being arranged adjacent to the inner volume of the microcavity,
    characterized in that
    the contact side of the electrode has a characteristic diameter D2 being larger than D1,
    the microcavity comprises an upper cavity section, which is limited upwardly by the microaperture surface and which has a characteristic diameter D3 in a cross section and in that the microcavity comprises a lower cavity section located below the upper cavity section and which has a characteristic diameter D4 in a cross section of the lower cavity, wherein D4>D3, and
    the upper cavity section has a characteristic height H3 and the lower cavity section has a characteristic height H4, wherein H4 is less than H3.

2. Microstructure apparatus according to claim 1, characterized in that D2 is larger than D1*1.5 (D1 multiplied by a factor c=1.5).

3. Microstructure apparatus according to claim 1 or 2, characterized in that the support substrate comprises a first layer, which is arranged substantially below the microaperture and inside of which the electrode is arranged.

4. Microstructure apparatus according to claim 3, characterized in that the support substrate comprises a second layer, which is arranged substantially below the microaperture and inside of which said microcavity is at least partially or substantially completely arranged.

5. Microstructure apparatus according to claim 4, characterized in that the microcavity is at least partially arranged also in the first layer.

6. Microstructure apparatus according to claim 1, characterized in that at least a portion of the contact side or the complete contact side has a micro-structured or nano-structured surface, or a micro-porous or nano-porous surface.

7. Method for the fabrication of a microstructure apparatus according to claim 1, comprising the following steps, in particular, without determining the order:
    providing a support substrate;
    applying at least one electrode onto the support substrate;
    applying a second layer above the support substrate;
    forming the at least one microcavity by selectively removing portions of said second layer, wherein said portions are forming the microcavity, at least in part or completely.

8. Method according to claim 7, wherein said second layer is formed directly on the support substrate, or alternatively, said layer is indirectly formed on the support substrate by first forming the layer on a second support substrate and second, transferring the layer from the second support substrate to the support substrate.

* * * * *